United States Patent
Aslanian

[11] Patent Number: 5,990,147
[45] Date of Patent: Nov. 23, 1999

[54] H₃ RECEPTOR LIGANDS OF THE PHENYL-ALKYL-IMIDAZOLES TYPE

[75] Inventor: Robert G. Aslanian, Rockaway, N.J.

[73] Assignee: Schering Corporation, Kenilworth, N.J.

[21] Appl. No.: 09/186,492

[22] Filed: Nov. 5, 1998

Related U.S. Application Data

[60] Provisional application No. 60/064,885, Nov. 7, 1997, and provisional application No. 60/095,357, Aug. 5, 1998.

[51] Int. Cl.⁶ .................. C07D 233/64; A61K 31/415
[52] U.S. Cl. ............................. 514/400; 548/346.1
[58] Field of Search ................... 548/346.1; 514/400

[56] References Cited

U.S. PATENT DOCUMENTS

| | | | |
|---|---|---|---|
| 5,559,113 | 9/1996 | Schwartz et al. | 514/400 X |
| 5,578,616 | 11/1996 | Aslanian et al. | 548/346.1 |
| 5,708,171 | 1/1998 | Schwartz et al. | 544/324 |
| 5,869,479 | 8/1997 | Kreutner et al. | 514/400 X |

FOREIGN PATENT DOCUMENTS

| | | |
|---|---|---|
| 93/12107 | 6/1993 | WIPO. |
| 93/12108 | 6/1993 | WIPO. |
| 93/14070 | 7/1993 | WIPO. |
| 95/06037 | 3/1995 | WIPO. |
| 95/14007 | 5/1995 | WIPO. |
| 96/29315 | 9/1996 | WIPO. |
| 98/06394 | 2/1998 | WIPO. |

OTHER PUBLICATIONS

Partial translation for WO 9629315, Sep. 1996.

*Primary Examiner*—Fiona T. Powers
*Attorney, Agent, or Firm*—Henry C. Jeanette

[57] ABSTRACT

Disclosed are novel phenyl-alkyl-imidazoles of the formula

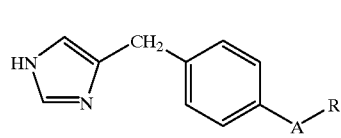

(I)

or pharmaceutically acceptable salts or solvates thereof, wherein A and R, are as defined in the specification.

Also disclosed are methods of treating allergy, inflammation, hypotension, glaucoma, sleeping disorders, states of hyper and hypo motility of the gastrointestinal tract, hypo and hyperactivity of the central nervous system, Alzheimer's, schizophrenia, obesity and migraines, comprising administering an effective amount of a compound of formula I (or a salt or solvate thereof) to a patient in need of such treatment.

Also disclosed are methods for treatment of upper airway allergic responses comprising administering a compound, or salt or solvate thereof, of formula I in combination or admixture with a histamine H₁ receptor antagonist.

13 Claims, No Drawings

$H_3$ RECEPTOR LIGANDS OF THE PHENYL-ALKYL-IMIDAZOLES TYPE

REFERENCE TO RELATED APPLICATIONS

This application claims the benefit of U.S. Provisional Application Ser. No. 60/064,885 filed Nov. 7, 1997, and U.S. Provisional Application Ser. No. 60/095,357 filed Aug. 5, 1998.

FIELD OF THE INVENTION

The present invention relates to phenyl-alkyl-imidazoles having valuable pharmacological properties, especially CNS activities and activity against inflammatory disease. Compounds of this invention are antagonists of the $H_3$ receptor.

BACKGROUND OF THE INVENTION

European Patent Application No. 0 420 396 A2 (Smith Kline & French Laboratories Limited) and Howson et al., *Bioorg. & Med. Chem. Letters*, Vol. 2 No. 1 (1992), pp. 77–78 describe imidazole derivatives having an amidine group as $H_3$ agonists. Van der Groot et al. (*Eur. J. Med. Chem.* (1992) Vol. 27, pp. 511–517) describe isothiourea analogs of histamine as potent agonists or antagonists of the histamine $H_3$ receptor, and these isothiourea analogs of histamine overlap in part with those of the two references cited above. Clapham et al. ["Ability of Histamine $H_3$ Receptor Antagonists to improve Cognition and to increase Acetylcholine Release in vivo in the Rat", British Assn. for Psychopharmacology, Jul. 25–28 1993, reported in *J. Psychopharmacol.* (Abstr. Book), A17] describe the ability of histamine $H_3$ receptor antagonists to improve cognition and to increase release of acetylcholine in vivo in the rat. Clapham et al. ["Ability of the selective Histamine $H_3$ Receptor Antagonist Thioperamide to improve Short-term Memory and Reversal Learning in the Rat", *Brit. J. Pharm. Suppl.*, 1993, 110, Abstract 65P] present results showing that thioperamide can improve short-term memory and reversal learning in the rat and implicate the involvement of $H_3$ receptors in the modulation of cognitive function. Yokoyama et al. ["Effect of thioperamide, a histamine $H_3$ receptor antagonist, on electrically induced convulsions in mice", *Eur. J. Pharmacol.*, vol. 234 (1993), pp. 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO9301812-A1 (SmithKline Beecham PLC) describes the use of S-[3-(4(5)-imidazolyl)propyl] isothiourea as a histamine $H_3$ antagonist, especially for treating cognitive disorders, e.g. Alzheimer's disease and age-related memory impairment. Schlicker et al. ["Novel histamine $H_3$ receptor antagonists: affinities in an $H_3$ receptor binding assay and potencies in two functional $H_3$ receptor models"] describe a number of imidazolylalkyl compounds wherein the imidazolylalkyl group is bonded to a guanidine group, an ester group or an amide group (including thioamide and urea), and compare these to thioperamide. Leurs et al. ["The histamine $H_3$-receptor: A target for developing new drugs", *Progr. Drug Res.* (1992) vol. 39, pp. 127–165] and Lipp et al. ["Pharmacochemistry of $H_3$-receptors" in "*The Histamine Receptor*, "eds.: Schwartz and Haas, Wiley-Liss, New York (1992), pp. 57–72] review a variety of synthetic $H_3$ receptor antagonists, and Lipp et al. (ibid.) have defined the necessary structural requirements for an $H_3$ receptor antagonist.

WO 95/14007 claims $H_3$ receptor antagonists of the formula

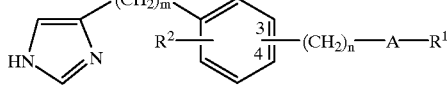

wherein

A is selected from $-O-CO-NR^1-$, $-O-CO-$, $-NR^1-CO-NR^1-$, $-NR^1-CO-$, $-NR^1-$, $-O-$, $-CO-NR^1-$, $-CO-O-$, and $-C(:NR^1)-NR^1-$;

the groups $R^1$, which may be the same or different when there are two or three such groups in the molecule of formula I, are selected from hydrogen, and lower alkyl, aryl, cycloalkyl, heterocyclic and heterocycloalkyl groups, and groups of the formula $-(CH_2)_y-G$, where G is selected from $CO_2R^3$, $COR^3$, $CONR^3R^4$, $OR^3$, $SR^3$, $NR^3R^4$, heteroaryl and phenyl, which phenyl is optionally substituted by halogen, lower alkoxy or polyhaloloweralkyl, and y is an integer from 1 to 3;

$R^2$ is selected from hydrogen and halogen atoms, and alkyl, alkenyl, alkynyl and trifluoromethyl groups, and groups of the formula $OR^3$, $SR^3$ and $NR^3R^4$;

$R^3$ and $R^4$ are independently selected from hydrogen, and lower alkyl and cycloalkyl groups, or $R^3$ and $R^4$ together with the intervening nitrogen atom can form a saturated ring containing 4 to 6 carbon atoms that can be substituted with one or two lower alkyl groups;

with the proviso that, when y is 1 and G is $OR^3$, $SR^3$ or $NR^3R^4$, then neither $R^3$ nor $R^4$ is hydrogen;

the group $-(CH_2)_n-A-R^1$ is at the 3- or 4-position, and the group $R^2$ is at any free position;

m is an integer from 1 to 3; and n is 0 or an integer from 1 to 3;

or a pharmaceutically acceptable acid addition salt thereof;

or a pharmaceutically acceptable salt thereof with a base when G is $CO_2H$; including a tautomeric form thereof.

The compounds are useful for treating various disorders, in particular such caused by allergy-induced responses.

U.S. application Ser. No. 08/689,951 filed Aug. 16, 1996 and U.S. application Ser. No. 08/909,319 filed Aug. 14, 1997 disclose compositions for the treatment of the symptoms of allergic rhinitis using a combination of at least one histamine $H_1$ receptor antagonist and at least one histamine $H_3$ receptor antagonist.

In view of the art's interest in compounds which affect the $H_3$ receptors, novel compounds having antagonist activity on $H_3$ receptors would be a welcome contribution to the art. This invention provides just such a contribution by providing novel compounds having $H_3$ antagonist activity.

SUMMARY OF THE INVENTION

It has now been found that members of a narrow group of compounds falling within the scope of WO 95/14007 but not specifically described therein are particularly active and show valuable pharmacological properties. The compounds are of the general formula

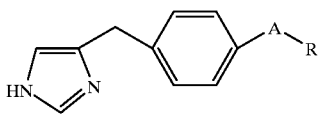

(I)

or a pharmaceutically acceptable acid addition salt or solvate thereof (or tautomer thereof, wherein:

A is —$CH_2$—NH—CO—NH—; —$CH_2$—O—CO—NH— or —$CH_2CH_2$—CO—NH—$(CH_2)_m$—;

m is 0, 1 or 2;

R is the group

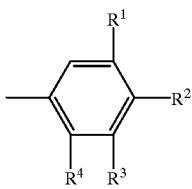

wherein at least two of $R^1$, $R^2$, $R^3$ and $R^4$ are hydrogen and the two others are independently selected from H, halogen (e.g., Br, I, F, or Cl), $CH_3$, $CF_3$, $OCH_3$, $OCF_3$ or CN; and with the proviso, that when A is —$CH_2$—O—CO—NH— and $R^1$, $R^3$ and $R^4$ are all hydrogen, then $R^2$ can not be Cl.

A further feature of the invention is pharmaceutical compositions containing as active ingredient a compound of the formula I defined above (or salt, or solvate or tautomer) together with a pharmaceutical carrier or excipient.

Further features of the invention are methods for treating allergy, (for example asthma), inflammation, cardiovascular disease, hypotension, raised intraocular pressure (such as glaucoma)—i.e., a method of lowering intraocular pressure, sleeping disorders (e.g., hypersomnia, somnolence, narcolepsy and sleeplessness, such as insomnia), diseases of the GI tract, states of hyper and hypo motility and acidic secretion of the gastrointestinal tract, disturbances of the central nervous system, hypo and hyperactivity of the central nervous system (for example, agitation and depression) and other CNS disorders (such as Alzheimer's, schizophrenia, obesity and migraine) comprising administering an effective amount of a compound of Formula I (or salt or solvate or tautomer thereof) to a patient in need of such treatment.

Another feature of this invention is a method for treating inflammation, which comprises administering to a patient suffering from inflammation an effective amount of a compound of formula I (or a salt, solvate or tautomer thereof) to a patient in need of such treatment.

Another feature of this invention is a method for treating allergy, which comprises administering to a patient suffering from allergy an effective amount of a compound of formula I (or a salt, solvate or tautomer thereof) to a patient in need of such treatment.

Another feature of this invention is a method for treating diseases of the GI-tract, which comprises administering to a patient suffering from a disease of the GI-tract an effective amount of a compound of formula I (or a salt, solvate or tautomer thereof) to a patient in need of such treatment.

Another feature of this invention is a method for treating cardiovascular disease, which comprises administering to a patient suffering from cardiovascular disease an effective amount of a compound of formula I (or a salt, solvate or tautomer thereof) to a patient in need of such treatment.

Another feature of this invention is a method for treating disturbances of the central nervous system, which comprises administering to a patient suffering from disturbances of the central nervous system an effective amount of a compound of formula I (or a salt, solvate or tautomer thereof) to a patient in need of such treatment.

The invention also includes the aspect of using the claimed compounds in combination with a histamine $H_1$ receptor antagonist for treatment of allergy-induced airway (e.g., upper airway) responses.

DETAILED DESCRIPTION OF THE INVENTION

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Numerous chemical substances are known to have histamine $H_1$ receptor antagonist activity. Many useful compounds can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine (also known as SCH-34117), diphenhydramine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

For example, the $H_3$ antagonists of this invention can be combined with an $H_1$ antagonist selected from astemizole, azatadine, azelastine, brompheniramine, cetirizine, chlorpheniramine, clemastine, carebastine, descarboethoxy-loratadine (also known as SCH-34117), diphenhydramine, doxylamine, ebastine, fexofenadine, loratadine, levocabastine, mizolastine, norastemizole, or terfenadine.

Also, for example, the $H_3$ antagonists of this invention can be combined with an $H_1$ antagonist selected from, azatadine, brompheniramine, cetirizine, chlorpheniramine, carebastine, descarboethoxyloratadine (also known as SCH-34117), diphenhydramine, ebastine, fexofenadine, loratadine, or norastemizole.

Representative combinations include: the $H_3$ antagonists of this invention with loratadine, $H_3$ antagonists of this invention with descarboethoxyloratadine, $H_3$ antagonists of this invention with fexofenadine, and $H_3$ antagonists of this invention with cetirizine.

Preferably, compound 8 is used in the methods of this invention.

Those skilled in the art will know that the term "upper airway" means the upper respiratory system—i.e., the nose, throat, and associated structures.

This invention includes compounds wherein at least two of $R^1$, $R^2$, $R^3$ and $R^4$ are hydrogen and the two others are independently selected from H, F, Cl, $CH_3$, $CF_3$, $OCH_3$, $OCF_3$ or CN.

This invention also includes compounds wherein at least two of $R^1$, $R_2$, $R^3$ and $R^4$ are hydrogen and the two others are Cl.

This invention further includes compounds wherein at least two of $R^1$, $R^2$, $R^3$ and $R^4$ are hydrogen and the two others are Cl, and A is —$CH_2$—NH—CO—NH—.

Representative compounds of the invention include:

1

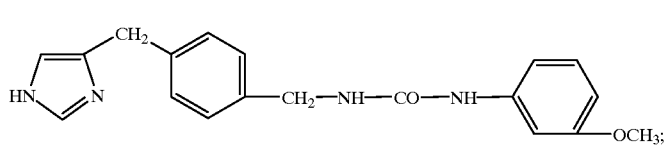

2

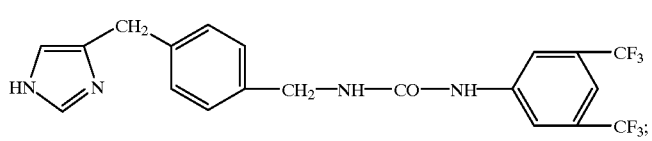

3

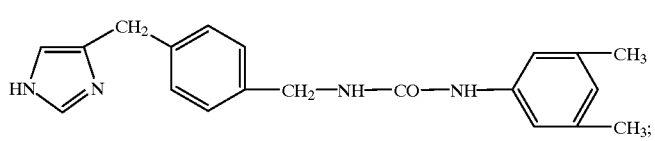

4

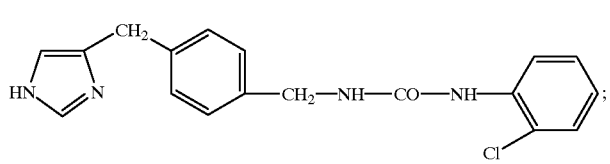

5

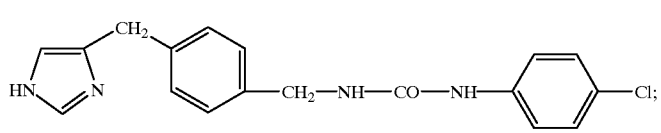

6

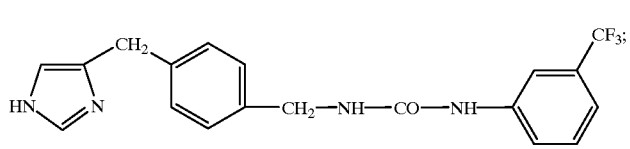

7

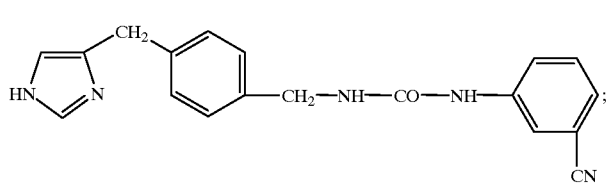

8

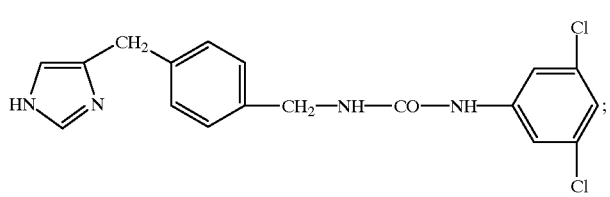

9
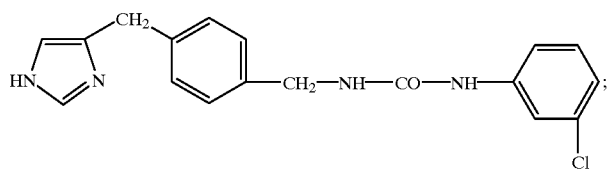
10
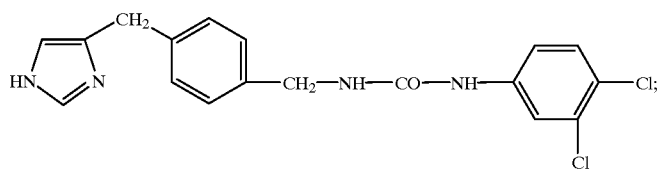
11
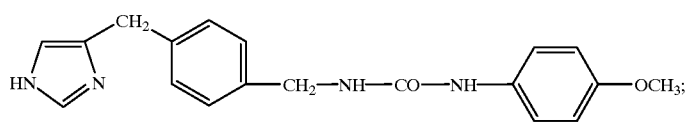
12
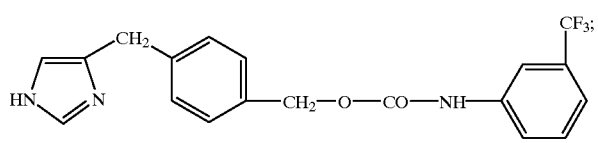
13
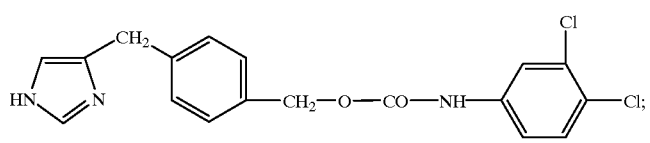
14
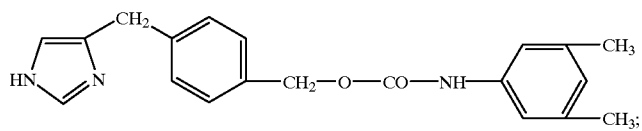
15
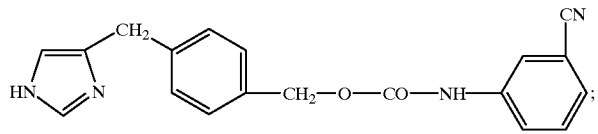
16
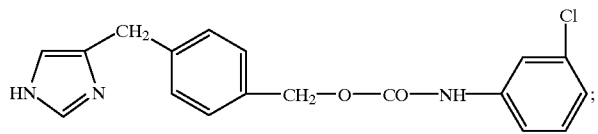
17
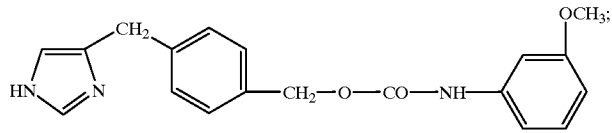
18
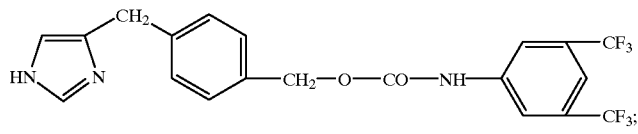

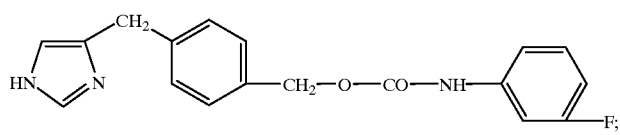

19

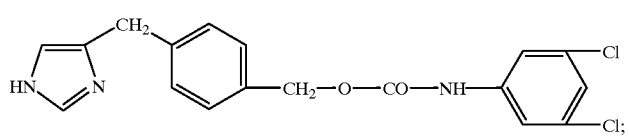

20

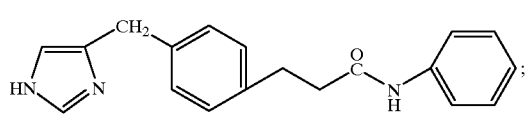

21

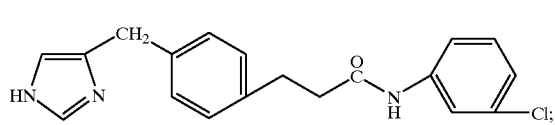

22

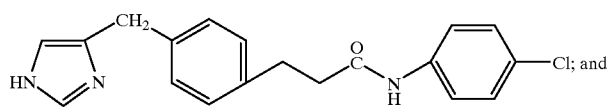

23

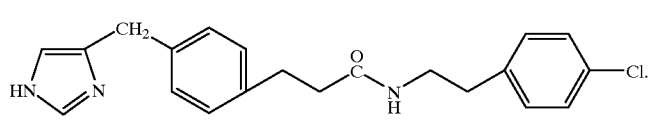

24

Preferably, the compound is compound 8 (see Example 3 below).

PROCESSES FOR PREPARING THE COMPOUNDS

Compounds of the formula I can be prepared by a process in which the left-hand part of the molecule represented by

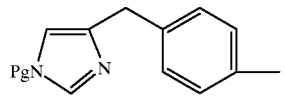

25 is coupled to a compound providing the remainder of the molecule, including the group R. Those skilled in the art will appreciate that Pg represents a suitable protecting group (e.g., trityl, abbreviated "Tr"). Specific examples of processes for the preparation of such compounds follow.

Process 1

For the preparation of a compound of the formula I wherein A is —CH$_2$—O—CO—NH—, reaction of a hydroxy compound with an isocyanate:

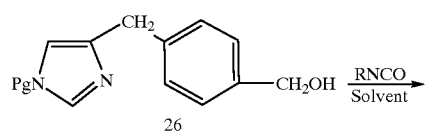

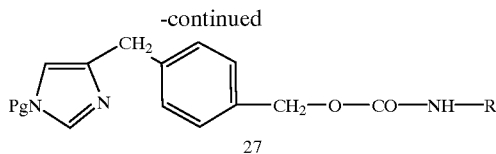

27

The hydroxy compound can be prepared by reaction of a compound of the formula 28 (wherein Y is CHO)

28 with a hydride reducing agent such as DiBALH, lithium aluminum hydride, sodium borohydride or the like.

Process 2

For the preparation of a compound of the formula I wherein A is —CH$_2$—NH—CO—NH—, reaction of an amino compound with an isocyanate:

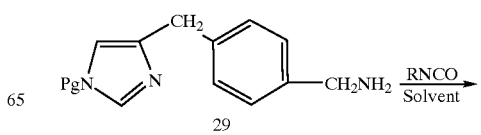

29

-continued

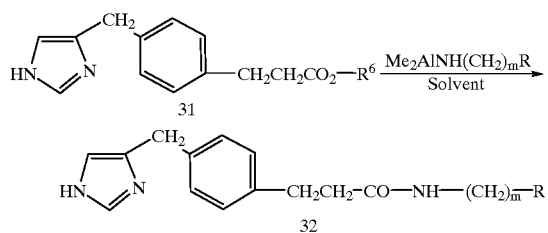
30

The amino compound can be prepared for example by reduction of a compound of the formula 28 wherein Y is CN with a hydride reducing agent such as lithium aluminum hydride, or by catalytic hydrogenation with e.g. Raney nickel or palladium on carbon.

Process 3

For the preparation of a compound of the formula I wherein A is —$CH_2$ $CH_2$—CONH—$(CH_2)_m$—, reaction of an ester with a dialkylaluminoamine, preferably one of the formula $Me_2AlNH$—$(CH_2)_m$—R

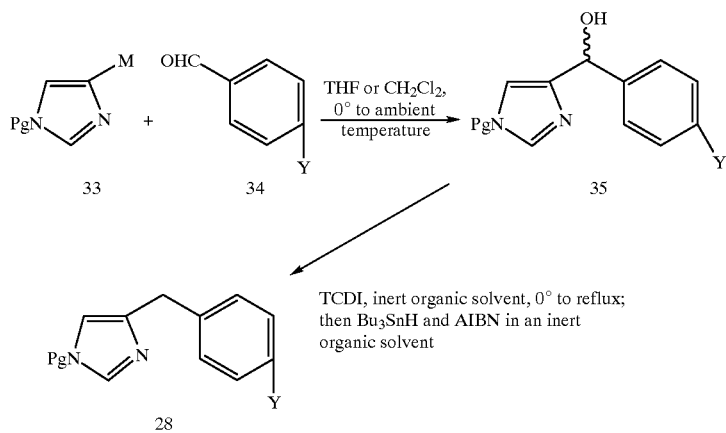

(wherein $R^6$ is a lower alkyl group, e.g., methyl or ethyl).

Preparation of Starting Materials and Intermediates

Starting materials for processes 1, 2 and 3 can be prepared by the methods discussed below, wherein: Y represents a group convertible into —$CH_2CH_2$—CO—$OR^6$, —$CH_2$—$NH_2$, or $CH_2OH$. In a first step compound 28 is prepared:

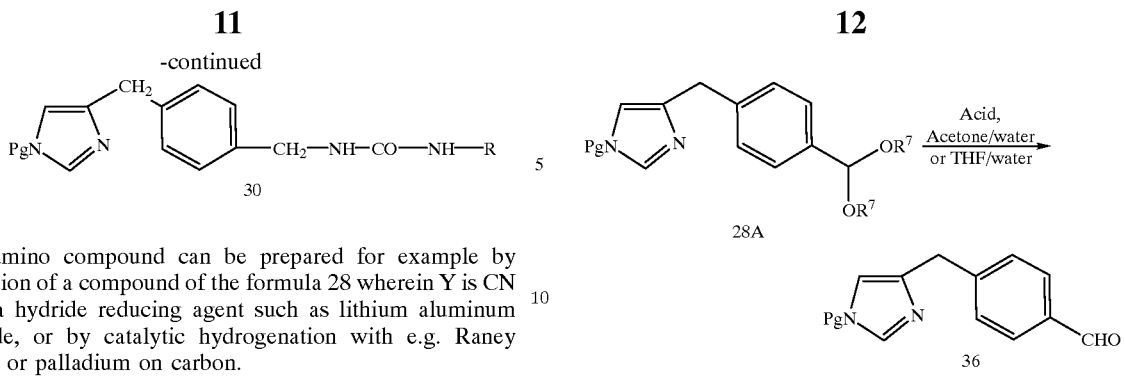

wherein $R^7$ is a lower alkyl group, e.g., methyl or ethyl. The aldehyde 36 is then converted into a starting compound for process 1 as described above.

For process 2, Y is preferably —$CH_2.NH_2$ which is obtained by reduction of the compound 28 wherein Y=CN, i.e., compound 28B

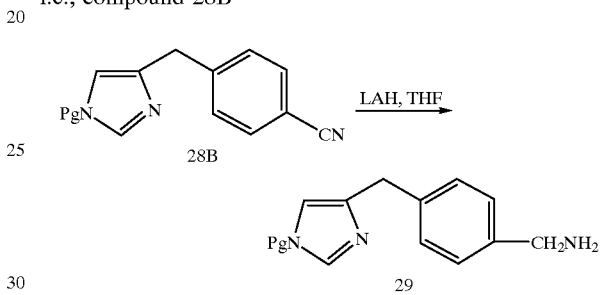

For compounds wherein Y is —$CH_2CH_2CO_2R^6$, the starting material is the acetal which can be converted as above to the corresponding aldehyde. The aldehyde is then reacted with the imidazole oganometallic reagent and the resulting alcohol reduced. The unsaturated compound is then reduced to —$CH_2CH_2$—$CO_2R^6$:

M stands for MgX (X=Br or I), Y stands for CN or $CH(OR)_2$, TCDI stands for thiocarbonyldiimidazole, and AIBN stands for azoisobutylnitrile.

For process 1, Y is preferably —$CH_2OH$. In a first step an aldehyde is formed:

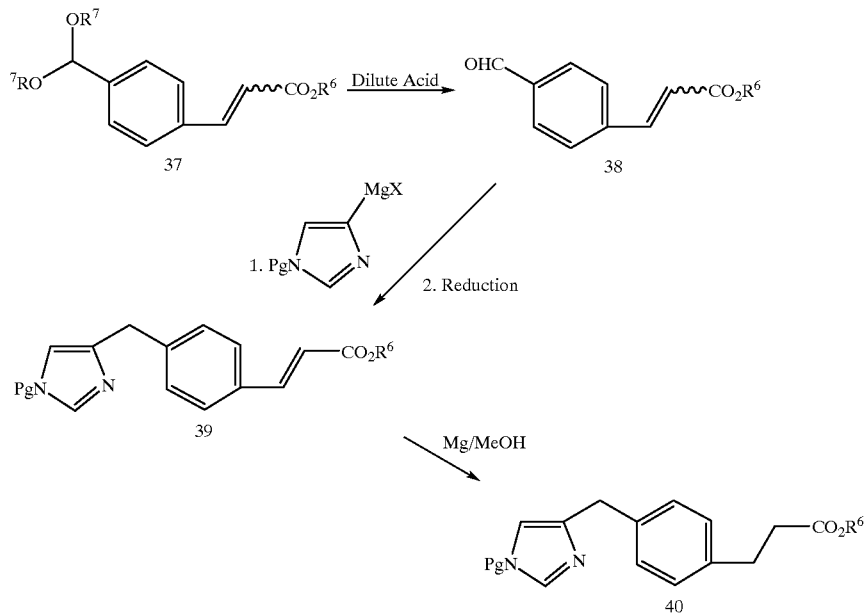

The resulting ester is then used as a starting compound for process 3.

Those skilled in the art will appreciate that the compound 37 can be prepared by treating

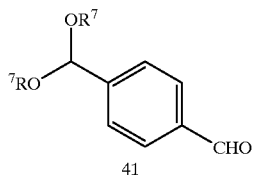

with a phosphorous ylide such as that generated from $(EtO)_2POCH_2CO_2R^6/NaN(SiMe_3)_2$.

The last step is mostly the deprotection of any protecting groups. This can be accomplished by several methods well known in the art. The protecting group is preferably one that can be removed by hydrolysis or hydrogenolysis; it can for example be a trityl group $(C_6H_5)_3C-$, which is preferably removed by hydrolysis in an aqueous organic solvent. The hydrolysis can for example be effected by means of mineral acid in an aqueous water-miscible organic solvent such as a lower alkanol, especially methanol or ethanol. Other protecting groups that can be used (and their method of removal) include t-Bu-OCO—[often abbreviated to t-BOC] (which can be removed with acid, or with hydrazine, ammonia and a lower alkanol, e.g., methanol or ethanol), and (2-triloweralkylsilyl)ethoxymethyl groups, especially $Me_3Si(CH_2)_2OCH_2-$ [often abbreviated to SEM] (which can be removed with acid or fluoride ion).

Compounds useful in this invention are exemplified by the following examples, which should not be construed to limit the scope of the disclosure.

EXAMPLE 1

Step 1

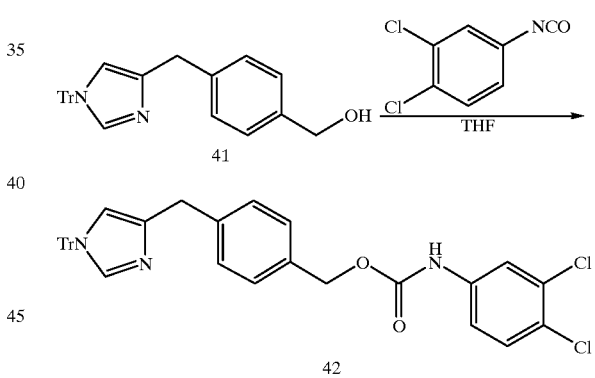

A solution of the alcohol 41 (0.3 gm, 0.7 mmols) and the isocyanate (0.16 gm, 0.84 mmols) in dry THF (10 ml) were stirred under a nitrogen atmosphere at 22° C. for 2 hr. The reaction was concentrated under reduced pressure, diluted with methylene chloride (50 ml) and washed with brine. The organic layer was separated, dried (Na$_2$SO$_4$), filtered, and concentrated under reduced pressure. The residue was purified on a Flash Column (1:1 hexane:ethyl acetate) to yield the product 42 as a white solid (0.4 gm, 92%).

Step 2

-continued

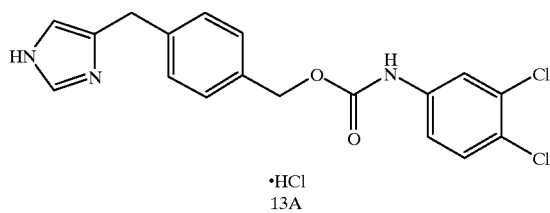

·HCl
13A

Compound 42 (0.4 gm, 0.65 mmols) in 3N HCl in methanol (40 ml) was heated to 60° C. under a nitrogen atmosphere for 2 hr. The reaction was cooled to 22° C. and concentrated under reduced pressure. The residue was dissolved in methanol (30 ml), neutralized with concentrated ammonium hydroxide, and reconcentrated. The residue was purified on a flash column (10% methanol saturated with ammonia in methylene chloride) to yield the product. This material was treated with 3N HCl (20 ml) to form the HCl salt 13A which was obtained as a white powder after concentration under reduced pressure (0.22 gm, 84%). Mass spec: (FAB) 376 (M+H).

EXAMPLE 2

Step 1

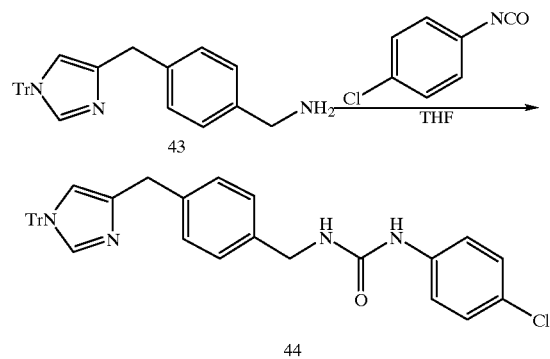

A solution of the amine 43 (0.32 gm, 0.75 mmol) in dry THF (4 ml) was added dropwise to a solution of the isocyanate (0.14 gm, 0.94 mmol) in THF (3 ml) under a nitrogen atmosphere at 22° C. Additional THF (3 ml) was used to rinse the flask and syringe. After 2 hr., TLC (5% methanol saturated with ammonia in methylene chloride) indicated complete consumption of the amine. The reaction was concentrated under reduced pressure and purified on a Flash column (120 gm silica gel; 2.5% methanol saturated with ammonia in methylene chloride) to yield a white foam (0.22 gm). The mixed fractions were repurified using the same conditions to yield additional product (0.14 gm; total yield=82%): Mass spec (FAB)=583 (M+1).

Step 2

-continued

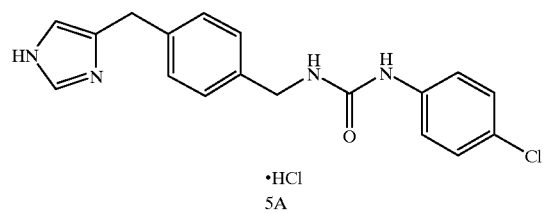

·HCl
5A

In a manner similar to that described for Example 1, Step 2, compound 44, from Step 1, (0.3 gm, 0.52 mmols) was converted to the product 5A (0.052 gm, 27%): Mass spec (Cl)=216 (7%), 188 (35%), 171 (87%), 154 (100).

EXAMPLE 3

Step 1

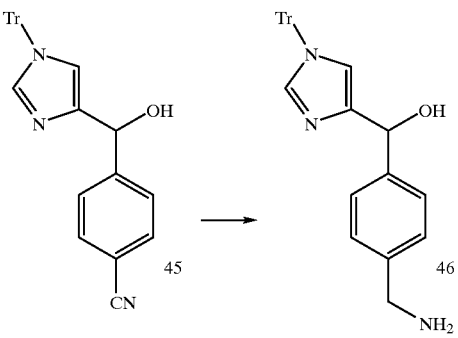

To a 1 L Parr flask containing 5.2 g of Raney nickel (washed with ethanol (4×10 mL)) was added 400 mL of $NH_3$ sat. methanol and 9.8 g of hydroxy nitrile compound 45 (22.2 mmol), and the mixture was hydrogenated at 45 psi $H_2$ for 8 h. The reaction mixture was filtered and concentrated. The product was purified by flash column (silica gel) eluting with 20:1:0.1 to 10:1:0.1 $CH_2Cl_2$—MeOH—$NH_3$ aq. to give 7.65 g of desired product 46 (17.2 mmol, 77% yield).

$^1$H-NMR (CD$_3$OD) 7.2–7.5 (20H, m), 6.84 (1H, s), 5.78 (1H, s), 5.78 (1H, s) and 3.82 (2H, s).

Step 2

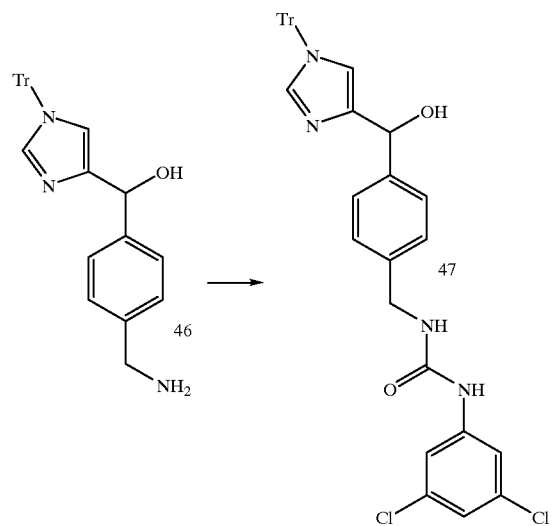

To a solution of compound 46 (7.65 g, 17.2 mmol) dissolved in THF (700 mL) was added a solution of 3,5- dichlorophenyl isocyanate (3.27 g, 17.4 mmol) dissolved in THF (50 mL). The reaction mixture was left stirring over night and concentrated to give clean crude product 47 as a white foam. The crude product was used in the next step without further purification.

$^1$H-NMR (CD$_3$OD and d$_6$-DMSO) 7.2–7.5 (22H, m), 7.08 (1H, s), 6.84 (1H, s), 5.77 (1H, s), 4.43 (2H, s).

Step 3

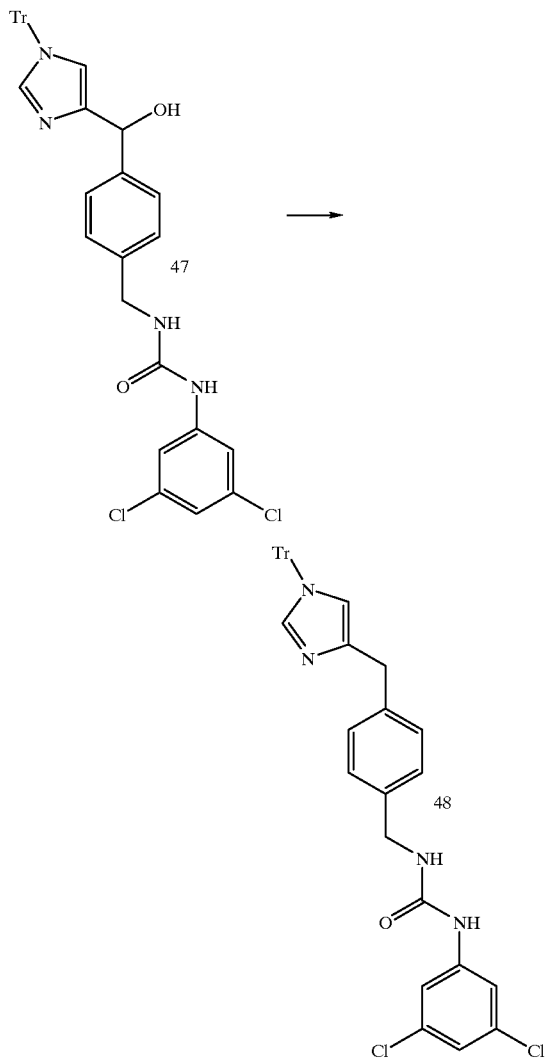

To a solution of crude compound 47 (~17.2 mmol) and NaI (21.5 g, 144 mmol) in CH$_2$Cl$_2$ (200 mL) and acetone (200 mL) was added 12.6 mL of dichloro dimethylsilane (103 mmol). After stirring at room temperature for 30 min, the reaction mixture was added to CH$_2$Cl$_2$ (500 mL) and washed with 10% sodium thiosulfate (500 mL, 4×250 mL), H$_2$O (250 mL) and brine (250 mL), dried with MgSO$_4$ and concentrated. The product was purified by flash column (silica gel) eluting with 50:1 to 20:1 CH$_2$Cl$_2$—MeOH to give 9.10 g of desired product 48 as a white solid (14.7 mmol, 86% yield for two steps).

$^1$H-NMR (CDCl$_3$) 8.71 (1H, s), 7.44 (1H, s), 7.1–7.4 (H, m), 6.88 (1H, s), 6.71 (1H, s), 5.99 1H, d, J=5.8 Hz), 4.15 (2H, d, J=5.8 Hz), 3.80 (2H, s).

Step 4

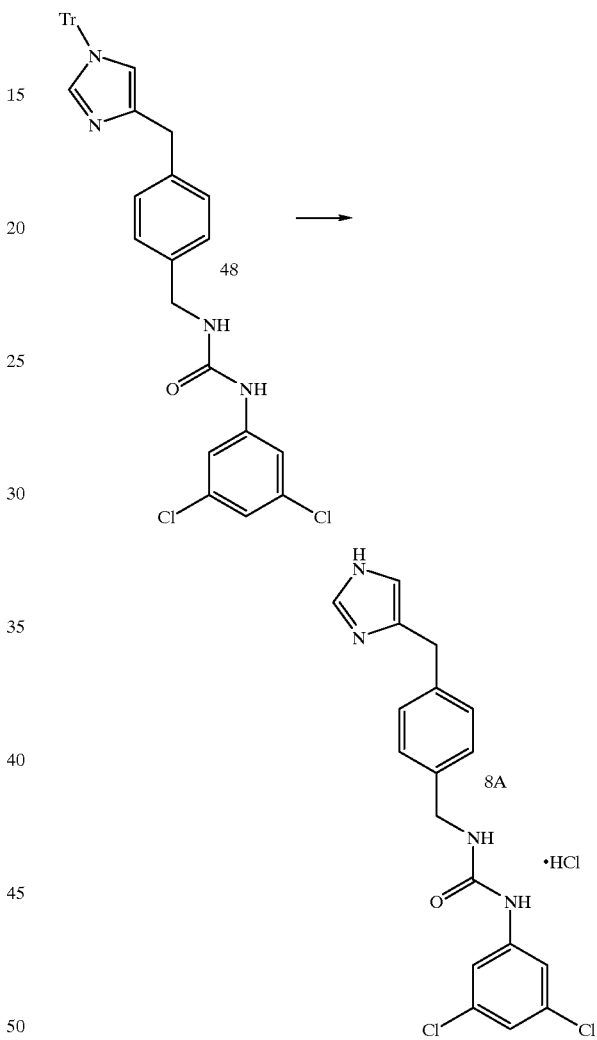

The trityl group was removed and converted to its HCl salt by standard procedures. The HCl salt was crystallized from EtOH-tert-butyl methyl ether to give desired product 8A white crystals (m.p. 182.5–184° C.).

HRMS (FAB, M+H$^+$): m/e calc'd for [C$_{18}$H$_{17}$Cl$_2$N$_4$O]$^+$: 375.0779, found 375.0787.

$^1$H-NMR (CD$_3$OD) 8.88 (1H, s), 7.50 (2H, d, J=1.8 Hz), 7.40 (2H, d, J=8.1 Hz), 7.37 (1H, s), 7.32 (2H, d, J=8.1 Hz), 7.05 (1H, t, J =1.8 Hz), 4.44 (2H, s), 4.15 (2H, s).

EXAMPLE 4

Step 1

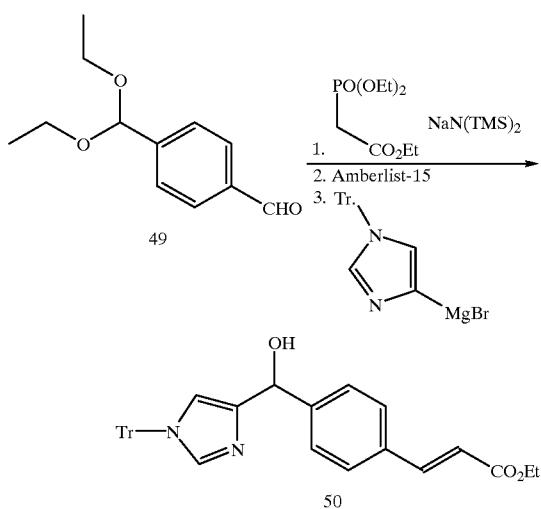

A solution of 1 M sodium bis(trimethylsilyl)amide in THF (110 ml, 110 mmol) cooled to 0° C. was treated with triethylphosphonoacetate (23.5 ml, 118 mmol). After 20 min. the reaction mixture was warmed to RT. and terephthalaldehyde mono-(diethyl acetal) (19.3 ml, 97.0 mmol) dissolved in THF (250 ml) was added over 25 min. The reaction mixture was stirred at 35° C. for 3.5 h and concentrated. The residue was suspended in EtOAc (250 ml), washed with $H_2O$ (100 ml) and brine (100 ml), dried with $MgSO_4$ and concentrated to give 27 g of crude intermediate.

The crude intermediate (27 g) was dissolved in acetone (350 ml) and $H_2O$ (4.5 ml), treated with Amberlyst-15 resin (3.1 g) for 2.5 h, filtered and concentrated to give the aldehyde intermediate.

To a cooled (0° C.) solution of 4-iodo-1-trityl imidazole (41.3 g, 96.9 mmol) in $CH_2Cl_2$ (500 ml) was added 3M EtMgBr in ether (35 ml, 105 mmol) over 15 min. After 30 min. at 0° C. the reaction mixture was warmed to RT. and a solution of the aldehyde intermediate in $CH_2Cl_2$ (50 ml) was added. After 2 h, the reaction mixture was added to 1 L of half sat. aqueous $NH_4Cl$. The organic layer was partitioned off and the aqueous layer was extracted with $CH_2Cl_2$ (3×200 ml). The combined organic layers were washed with brine (250 ml), dried with $MgSO_4$ and concentrated. The product was purified by silica gel chromatography eluting with 1:1 $CH_2Cl_2$-EtOAc to give 30.2 g of product 50 (59 mmol, 61% overall yield): $^1$H-NMR (CDCl$_3$) δ 1.34 (t, J=7.1 Hz, 3H), 4.26 (q, J=7.1 Hz, 2H), 5.79 (s, 1H), 6.40 (d, J=16.0 Hz, 1H), 6.59 (s, 1H), 7.1–7.5 (m, 20H), 7.65 (d, J=16.0 Hz, 1H).

Step 2

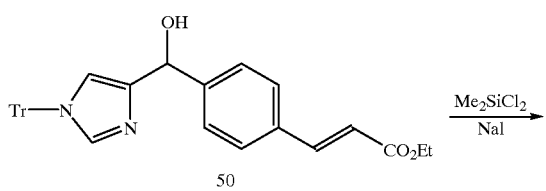

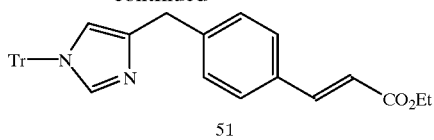

To a solution of compound 50 (10.2 g, 19.9 mmol), $CH_2Cl_2$ (115 ml), acetone (115 ml) and NaI (11.9 g, 79.3 mmol) was added dichlorodimethylsilane (19.4 ml, 159 mmol). After 15 min. the reaction mixture was added to $CH_2Cl_2$ (600 ml) and washed with 10% aqueous sodium thiosulfate (5×400 ml), $H_2O$ (2×400 ml) and brine (400 ml), dried with $MgSO_4$ and concentrated. The product was purified by silica gel chromatography eluting with 2:1 followed by 1:1 $CH_2Cl_2$-EtOAc to give 7.2 g of product 51 (14 mmol, 72% yield). $^1$H-NMR (CDCl$_3$) δ 1.33 (t, J=7.0 Hz, 3H), 3.90 (s, 2H), 4.26 (q, J=7.0, 2H), 6.39 (d, J=16.0 Hz, 1H), 6.58 (s, 1H), 7.1–7.5 (m, 20H), 7.65 (d, J=16.0 Hz, 1H).

Step 3

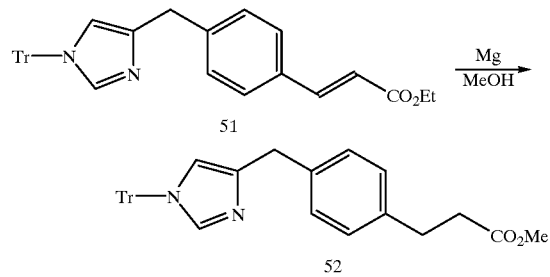

To a suspension of compound 51 (6.2 g, 12 mmol) in MeOH (65 ml) was added magnesium (0.65 g, 27 mmol), stirred at RT. for 2 h. More magnesium (0.71 g, 29 mmol) was added and the reaction mixture was stirred an additional 1.5 h. The reaction mixture was added to 3M HCl (80 ml) and extracted with $CH_2Cl_2$ (3×50 ml). The combined organic layers were washed with brine (60 ml), dried with $MgSO_4$, concentrated and purified by silica gel chromatography eluting with 30:1 to 10:1 $CH_2Cl_2$:MeOH to give 5.0 g of the saturated methyl ester intermediate 52 (10 mmol, 86% yield). $^1$H-NMR (CDCl$_3$) δ 2.60 (t, J=7.4 Hz, 2H), 2.91 (t, J=7.4 Hz, 2H), 3.67 (s, 3H), 3.87 (s, 2H), 6.56 (s, 2H), 7.1–7.4 (m, 20H)

Step 4

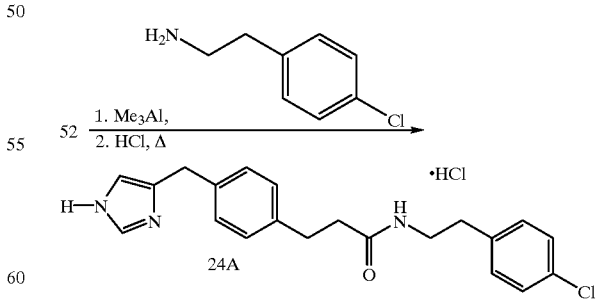

To a cooled (0° C.) solution of 2(4-chlorophenyl) ethylamine (76 μl, 0.57 mmol) in toluene (10 ml) was added 2M trimethyl aluminum in toluene (0.55 ml, 1.1 mmol) and stirred at RT. for 45 min. To the reaction mixture was added a solution of compound 52 (0.28 g, 0.54 mmol) in toluene (5.0 ml). After heating at 65° C. for 3.5 h, the reaction mixture was cooled, carefully quenched with sat. $Na_2SO_4$ (aq.), concentrated and purified by silica gel chromatography eluting with 5% $NH_3$ sat. MeOH in $CH_2Cl_2$ to give 0.16 g of the amide intermediate (0.26 mmol, 48% yield).

A solution of the amide intermediate (0.16 g, 0.26 mmol) in EtOH (5.0 ml) was treated with 3M HCl (5.0 ml) at 65° C. for 2 h and concentrated. Purification by silica gel chromatography eluting with 5% $NH_3$ sat. MeOH in $CH_2Cl_2$ followed by acidification with 3M HCl and concentration gave 35 mg of the titled product 24A (0.095 mmol, 37% yield). HRMS $(M+H^+)$: m/e calc'd $[C_{21}H_{23}N_3OCl]^+$: 368.1533, found 368.1530.

Following the examples above using the appropriate starting compounds and reaction conditions suitable for the compounds used compounds 1–4, 6, 7, 9–12, and 14–23 described above were prepared as their HCl salt. The results of mass spectrometry run on the HCl salts are given in the table below.

Physical Data

| Compound # | Mass. Spec Data | Compound # | Mass. Spec Data |
|---|---|---|---|
| 1 | (FAB) 337 (M + 1) | 14 | (FAB) 336 (M + 1) |
| 2 | (FAB) 443 (M + 1) | 15 | (FAB) 333 (M + 1) |
| 3 | (FAB) 335 (M + 1) | 16 | (FAB) 342 (M + 1) |
| 4 | (CI) 341 (M + 1) | 17 | (FAB) 338 (M + 1) |
| 6 | (FAB) 375 (M + 1) | 18 | (FAB) 444 (M + 1) |
| 7 | (FAB) 332 (M + 1) | 19 | (CI) 326 (M + 1) |
| 9 | (FAB) 341 (M + 1) | 20 | (CI) 376 (M + 1) |
| 10 | (FAB) 375 (M + 1) | 21 | (CI) 306 (M + 1) |
| 11 | (FAB) 391 (M + 1) | 22 | (CI) 340 (M + 1) |
| 12 | (EI) 375 (M+) | 23 | (FAB) 354 (M + 1) |

It has surprisingly been found that these selection compounds are in general substantially more active than the preferred compounds of WO 95/14007. However, their most substantial advantage is that they provide higher blood levels of the compound and are believed to be more bioavailable more easily absorbed orally. This make them particularly useful as medicaments.

$H_3$-Receptor Binding Assay

The source of the $H_3$ receptors in this experiment was guinea pig brain. The animals weighed 400–600 g. The brain tissue was homogenized using a Polytron in a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 µg/ml with 0.1% DMSO. Membranes were then added (400 µg of protein) to the reaction tubes. The reaction was started by the addition of 3 nM [$^3$H]R-a-methylhistamine (8.8 Ci/mmol) or 3 nM [$^3$H]$N^a$-methylhistamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM). The results are given in the table below for the HCl salt of the indicated compound.

| Compound # | $K_i$ (nM) | Compound # | $K_i$ (nM) |
|---|---|---|---|
| 1 | 18 | 14 | 17 |
| 2 | 22 | 15 | 7 |
| 3 | 9 | 16 | 7 |
| 4 | 32 | 17 | 13 |
| 5 | 21 | 18 | 23 |
| 6 | 16 | 19 | 5 |
| 7 | 5 | 20 | 5 |
| 8 | 4, 12 | 21 | 2 |
| 9 | 6 | 22 | 1 |
| 10 | 7 | 23 | 29 |
| 11 | 5 | 24 | 5 |
| 12 | 21 | — | — |
| 13 | 18 | — | — |

From these test results and the background knowledge about the compounds described in the references in the section "Background of the Invention", it is to be expected that the compounds of the invention would be useful in treating inflammation, allergy, diseases of the GI-tract, cardiovascular disease, or disturbances of the central nervous system.

Pharmaceutically acceptable inert carriers used for preparing pharmaceutical compositions from the compounds of Formula I and their salts can be either solid or liquid. Solid form preparations include powders, tablets, dispersible granules, capsules, cachets and suppositories. The powders and tablets may comprise from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

Liquid form preparations include solutions, suspensions and emulsions, for example water or water-propylene glycol solutions for parenteral injection. Liquid form preparations may also include solutions for intranasal administration.

Also included are solid form preparations which are intended for conversion, shortly before use, into liquid form preparations for either oral or parenteral administration. Such liquid forms include solutions, suspensions and emulsions.

Aerosol preparations suitable for inhalation may include solutions and solids in powder form, which may be in combination with a pharmaceutically acceptable carrier, such as an inert compressed gas.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, and allowed to cool and thereby solidify.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose. The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. The determination of the proper dosage for a particular condition is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 1 mg to 2000 mg/day, preferably 10 to 1000 mg/day, in one to four divided doses to achieve relief of the symptoms. The compounds are non-toxic when administered at therapeutic doses.

The following are examples of pharmaceutical dosage forms which contain a compound of the invention. As used therein, the term "active compound" is used to designate one of the compounds of the formula I or salt thereof.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade, | 45 | 40 |
| 5. | Magnesium Stearate | 3 | 7 |
|  | Total | 300 | 700 |

Method of Manufacture

Mix Items No. 1 and 2 in a suitable mixer for 10 to 15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1 to 3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |

-continued

| No. | Ingredient | mg/capsule | mg/capsule |
|---|---|---|---|
| 4. | Magnesium Stearate NF | 4 | 7 |
|  | Total | 250 | 700 |

Method of Manufacture

Mix Items No. 1, 2 and 3 in a suitable blender for 10 to 15 minutes. Add Item No. 4 and mix for 1 to 3 minutes. Fill the mixture into suitable two-piece hard gelatin capsules on a suitable encapsulating machine.

While a number of embodiments of this invention are described herein, it is apparent that the embodiments can be altered to provide other embodiments that utilize the compositions and processes of this invention. Therefore, it will be appreciated that the scope of this invention includes alternative embodiments and variations which are defined in the foregoing Specification and by the Claims appended hereto; and the invention is not to be limited to the specific embodiments that have been presented herein by way of example.

What is claimed is:

1. A compound of the formula

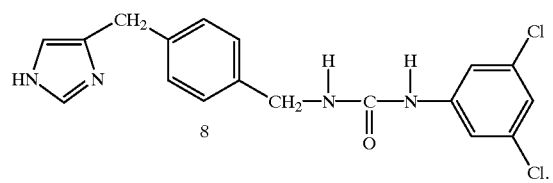

2. A pharmaceutical composition comprising an effective amount of a compound of claim 1, or a salt or solvate thereof, in combination with a pharmaceutically acceptable carrier.

3. A method of treating allergy, inflammation, hypotension, glaucoma, sleeping disorders, states of hyper and hypo motility of the gastrointestinal tract, hypo and hyperactivity of the central nervous system, Alzheimer's, Schizophrenia, obesity and migraines, comprising administering an effective amount of a compound, or a salt or solvate thereof, of claim 1 to a patient in need of such treatment.

4. A method for treating inflammation, which comprises administering to a patient suffering from inflammation an effective amount of a compound, or salt or solvate thereof, of claim 1.

5. A method for treating allergy, which comprises administering to a patient suffering from allergy an effective amount of a compound, or salt or solvate thereof, of claim 1.

6. A method for treating diseases of the GI-tract, which comprises administering to a patient suffering from a disease of the GI-tract an effective amount of a compound, or salt or solvate thereof, of claim 1.

7. A method for treating cardiovascular disease, which comprises administering to a patient suffering from cardiovascular disease an effective amount of a compound, or salt or solvate thereof, of claim 1.

8. A method for treating disturbances of the central nervous system, which comprises administering to a patient suffering from disturbances of the central nervous system an effective amount of a compound, or salt or solvate thereof, of claim 1.

9. A method for treatment of upper airway allergic responses comprising administering a compound, or salt or solvate thereof, of claim 1 in combination or admixture with a histamine $H_1$ receptor antagonist.

10. The method of claim 9 wherein said $H_1$ antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

11. The method of claim 10 wherein said $H_1$ antagonist is selected from: loratadine, descarboethoxyloratadine, fexofenadine, cetirizine.

12. The method of claim 11 wherein said $H_1$ antagonist is loratadine.

13. The method of claim 11 wherein said $H_1$ antagonist is descarboethoxyloratadine.

\* \* \* \* \*